United States Patent [19]

White

[11] 3,931,137

[45] Jan. 6, 1976

[54] HERBICIDAL COMPOSITIONS

[75] Inventor: Brian Graham White, Bracknell, England

[73] Assignee: Imperial Chemical Industries Limited, London, England

[22] Filed: May 22, 1974

[21] Appl. No.: 472,513

Related U.S. Application Data

[63] Continuation of Ser. No. 703,532, Feb. 7, 1968, abandoned.

[30] Foreign Application Priority Data

Feb. 24, 1967 United Kingdom............... 8854/67

[52] U.S. Cl................................ 260/96.5 R; 71/94
[51] Int. Cl.² ........................................ C07B 21/00
[58] Field of Search....................... 260/96.5, 96.5 R

[56] References Cited

UNITED STATES PATENTS

| | | | |
|---|---|---|---|
| 2,830,039 | 4/1958 | Weitkamp et al. | 260/96.5 |
| 2,972,528 | 2/1961 | Brian et al. | 71/2.5 |
| 3,340,041 | 9/1967 | Homer et al. | 71/94 |

*Primary Examiner*—Delbert E. Gantz
*Assistant Examiner*—C. E. Spresser
*Attorney, Agent, or Firm*—Cushman, Darby & Cushman

[57] ABSTRACT

A solid complex of a herbicidal bipyridylium salt in combination with urea or thiourea having the formula:

$X(A)_n(H_2O)_m$ 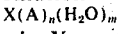

wherein X represents the bipyridylium salt, A represents urea or thiourea, $n$ is 1, 2 or 4, and $m$ is 0 to 4, its preparation and use are disclosed.

6 Claims, No Drawings

HERBICIDAL COMPOSITIONS

This is a continuation of application Ser. No. 703,532 filed Feb. 7, 1968, now abandoned.

This invention relates to novel compositions containing a herbicidal bipyridylium salt, their preparation and use. Bipyridylium salt herbicides have previously been made available for use in the form of aqueous solutions containing wetting agents and/or corrosion inhibitors, as described in British Pat. Nos. 813,531 and 913,413.

According to the present invention there is provided a solid complex of a herbicidal bipyridylium salt with urea or thiourea. More particularly there is provided a solid complex of a herbicidal bipyridylium salt having the formula:

$$X(A)_n(H_2O)_m$$

where X represents a herbicidal bipyridylium salt, A represents urea or thiourea, $n$ is 1, 2 or 4 and $m$ is an integer from 0 to 4. The complexes are solid crystalline materials and are generally coloured white or yellow. Examples of herbicidal bipyridylium salts forming such complexes include the following:

1,1'-ethylene-2,2'-bipyridylium dibromide
1,1'-dimethyl-4,4'-hipyridylium dichloride
1,1'-di-2-hydroxyethyl-4,4'-bipyridylium dichloride
1,1'-bis-3,5-dimethylmorpholinocarbonylmethyl-4,4'-bipyridylium dichloride
1-(2-hydroxyethyl)-1'-methyl-4,4'-bipyridylium dichloride
1,1'-di-carbamoylmethyl-4,4'-bipyridylium dichloride
1,1'-di-N-methylcarbamoylmethyl-4,4'-bipyridylium dichloride
1,1'-bis-N,N-dimethylcarbamoylmethyl-4,4'-bipyridylium dichloride
1,1'-diacetonyl-4,4'-bipyridylium dichloride
1,1'-diethoxycarbonylmethyl-4,4'-bipyridylium dibromide
1,1'-diallyl-4,4'-bipyridylium dibromide The bipyridylium salts listed above are all chorides or bromides, in which form they are most commonly encountered. However, many other salts, for example the iodide, methylsulphate, or p-toluenesulphonate, may be employed in forming the complexes of the invention. The 1,1'-dimethyl-4,4'-bipyridylium ion may also be referred to by its alternative name "paraquat" ion. Thus the second compound in the list above may be referred to as paraquat dichloride.

The complexes are conveniently obtained by adding urea or thiourea, in at least the stoichiometric quantity necessary to form the complex, to an aqueous solution of the bipyridylium salt. Solvents other than water, for example methanol or ethanol, may also be employed in preparing the complexes of the invention. Where an aqueous solution is used, its termperature may be any temperature between 0° and 100°C, but may conveniently be the temperature of the room in which the preparation is carried out.

In order to obtain solid compositions readily without the need for concentrating the reaction liquors by evaporation, the urea or thiourea is preferably added to a hot solution of bipyridylium salt in which the ion concentration exceeds the following limits.

a. 1,1'-dimethyl-4,4'-bipyridylium ion: 10%
b. 1,1'-di-2-hydroxyethyl-4,4'-bipyridylium ion: 10%
c. 1,1'-bis-3,5-dimethylmorpholinocarbonylmethyl-4,4'-bipyridylium ion: 20%
d. 1,1'-ethylene-2,2'-bipyridylium ion: 20%

Crystallisation occurs on cooling, but is rather slow when using dilute aqueous liquors.

It is often desirable to incorporate a suitable wetting agent in bipyridylium salt herbicides, and such wetting agents may be added to the hot aqueous bipyridylium salt solution before the addition of the urea or thiourea complexing agent.

The solids resulting are white or yellow-brown crystalline materials, which incorporate the bulk of the water originally present in the bipyridylium salt solution as lattice hydration. Generally they can be pressed sufficiently free from residual water to yield an easily handleable crystalline product.

If desired the solid complex may be freed from water by conventional drying techniques; for example, drying for a few hours at 80°C proves sufficient in some cases to cause virtually complete dehydration. This is important where solids containing a high concentration of bipyridylium ion are required, so that the cost of bulk transport may be minimised. Thus, for example, 30% aqueous solutions of 1,1'-dimethyl-4,4-bipyridylium ion can be converted into solid formulations with very little reduction in ion concentration when a small excess of thiourea is used, and moreover with an increase in ion concentration when the stoichiometric quantity is used: i.e. 33% paraquat ion concentration solids being obtained. The materials resulting from such treatments are very easily handled, free running systems, which dissolve quite readily in cold water in the proportion required for most applications. They can be converted to coloured solids by the addition of small quantities of suitable dyestuffs at the pre-crystallisation stage.

When making urea/bipyridylium salt complexes it is generally desirable to use more urea than the stoichiometric amount to form the complex, in order to precipitate the complex from solution more easily.

If desired, one can also prepare mixed urea/thiourea complexes in an analogous fashion. If desired, the solid complexes may be diluted with inert fillers.

Suitable inert fillers include potassium chloride, potassium nitrate, sodium sulphate, magnesium sulphate and sucrose.

Solid complexes associated with inert filler may be prepared by:

a. adding, if desired, a surfactant-wetter component to the hot aqueous bipyridylium salt solution,
b. maintaining the solution at an elevated temperature whilst solid urea and/or thiourea is added, and
c. maintaining the solution sufficiently hot to prevent solidification, where such may occur, whilst solid inert filler is added and dissolved.

The quantities of urea and/or thiourea, and inert filler which are added may be varied over quite large ranges, depending somewhat upon the complex and filler system being used.

Notably good results are obtainable by using as fillers the lower hydrated and anhydrous forms of magnesium sulphate. For example, when bipyridylium salt liquor — magnesium sulphate — urea/thiourea formulations are prepared, then allowed to stand in open shallow dishes, solidification can occur very rapidly, for example in less than 5 minutes. In this fashion solid blocks are obtainable. By varying the quantities of magnesium sulphate added one can vary the hardness of the formulations — the lower the quantity of magnesium sulphate added the softer the product, and the higher the overall bipyridylium ion concentration If during the cooling process the surface of the solution is agitated, small granules can be formed. These solid compositions can, if desired, be freed from water by conventional drying techniques.

The formulations produced with magnesium sulphate with or without drying dissolve in cold water rapidly, and very rapidly in warm water. Moreover, allowing for the variation of hardness with magnesium sulphate content, both dried and undried treatments yield easily handleable yellow-brown solids, with bipyridylium ion concentration of the order of 20—30% by weight but with drying manipulable up to about 35%.

As with the complexes, dried or undried "filled" systems may be coloured by the incorporation of small quantities of suitable dyestuffs.

| e.g. | lemon chrome | — | bright yellow |
| | brilliant yellow | | |
| | brilliant green | — | green |
| | tolylene blue | — | blue-green |
| | acridin red | — | scarlet red |

These dyes if required should be incorporated at the precrystallisation stage. The resultant solutions prepared by dissolution of these solid compositions in water are of the same colour as the solid substance.

The solid colorations could be used as a colour code indication of bipyridylium ion concentration for use in both agricultural and horticultural applications.

Herbicidal compositions as described above have a number of advantages. Thus, in some cases, in comparison with the bipyridylium salt from which they are drived, the urea and the thiourea complexes of this invention are effective in controlling the growth of unwanted vegetation for longer periods.

A second advantage is that these compositions, being solid, may be transported in plastic or paper sacks rather than water-tight containers. A third advantage is that they may be prepared without the use of special machinery (i.e. for granulating). Another advantage is that aqueous formulations of the complexes have reduced corrosivity. Thiourea, in particular, has been found to be an excellent corrosion inhibitor, and for this reason it is desirable, although not essential, that all compositions should contain a proportion of thiourea. Although this feature is not required insofar as the compositions of the invention can be transported in non-metallic containers, it is potentially useful in preventing corrosion of metallic spray equipment.

The following Examples 1–7 illustrate as one aspect of the invention the preparation of urea or thiourea complexes of bipyridylium salts.

EXAMPLE 1

This Example illustrates the preparation of 1,1'-dimethyl-4,4'-bipyridylium dichloride:thiourea having the formula:

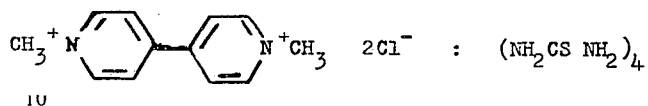

1,1'-Dimethyl-4,4'-bipyridylium dichloride dihydrate (1.0 g.) was suspended in refluxing ethanol (20 ml.). Thiourea (2.0 g.) was added, producing a yellow colouration in solution together with a yellow solid. The solution was filtered hot to yield a crude solid with melting point 164°–172°C. Recrystallisation from methanol yielded 1.8 g. of the complex. The melting point was found to be 160°–161°C. The results of the elemental analysis of the complex were as follows:

Found: C, 31.7; H, 5.0; N, 24.6; Cl, 12.8; S, 24.5%.
The above formula requires: C, 34.2; H, 5.3; N, 25.0; Cl, 12.7; S, 22.8%.

EXAMPLE 2

This Example illustrates the preparation of 1,1'-di-2-hydroxyethyl-4,4'-bipyridylium dichloride:thiourea having the formula:

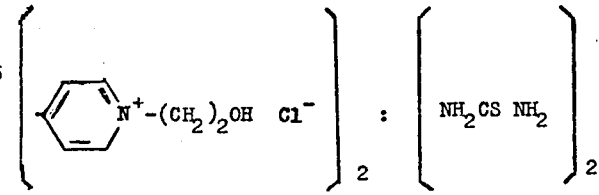

Thiourea (1.5 g.) was dissolved in hot ethanol (20 ml.) and then added to a solution of 1,1'-di-2-hydroxyethyl-4,4'-bipyridylium dichloride (1.6 g.) in hot aqueous ethanol, ($H_2O$-1 ml. plus ethanol 20 ml.). This treatment produced an orange solution which deposited yellow crystals on cooling. The yield of the complex was 1.6 g. The complex was recrystallised from aqueous ethanol and was then found to have a melting point of 144°–145°C. The results of the elemental analysis of the complex were as follows:

Found: C, 40.0; H, 4.1; N, 17.8; S, 14.2%. The above formula requires: C, 41.0; H, 4.1; N, 18.0; S, 13.8%.

EXAMPLE 3

This Example illustrates the preparation of 1,1'-bis-3,5-dimethylmorpholinocarbonylmethyl-4,4'-bipyridylium dichloride: thiourea, having the formula:

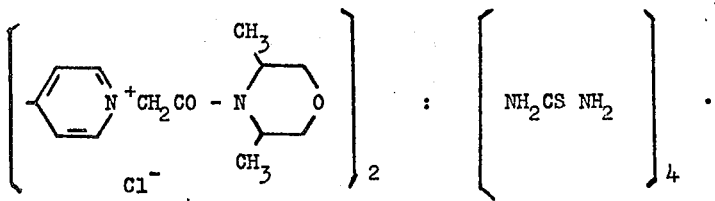

1,1′-Bis-3,5-dimethylmorpholinocarbonylmethyl-4,4′-bipyridylium dichloride (2.66 g.) was dissolved in hot methanol (20 ml.), and a saturated solution of thiourea (1.52 g.) in methanol was added. An orange solution was produced, which upon evaporation to dryness deposited orange rather hygroscopic crystals. The crude product was recrystallised from ethanol to yield orange crystals of the complex (2.0 g.). The melting point of the complex was found to be 173°–174°C. The results of the elemental analysis of the complex were as follows:

Found: C, 41.0; H, 6.1; N, 18.2; S, 15.0%. The above formula requires: C, 42.7; H, 6.2; N, 20.0; S, 15.2%.

EXAMPLE 4

This Example illustrates the preparation of 1,1′-ethylene-2,2′-bipyridylium dibromide:thiourea having the formula:

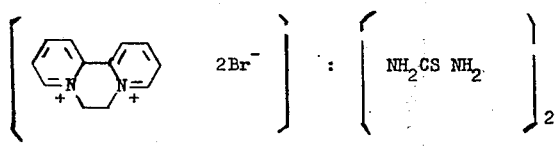

1,1′-Ethylene-2,2′-bipyridylium dibromide (1.0 g.) was dissolved in hot methanol (15 ml.). To this solution was added a hot saturated solution of thiourea (1.0 g.) in methanol. An orange solution was produced which on cooling deposited light yellow crystals. The yield of the complex was 1.0 g., and its melting point was found to be 105°–107°C. The material was recrystallised from methanol. The results of the elemental analysis of the complex were as follows:

Found: C, 33.1; H, 4.0; N, 16.7; S, 13.0%. The above formula requires: C, 33.8; H, 4.0; N, 16.8; S, 12.8%.

EXAMPLE 5

The preparation of 1,1′-dimethyl-4,4′-bipyridylium dichloride: urea having the formula:

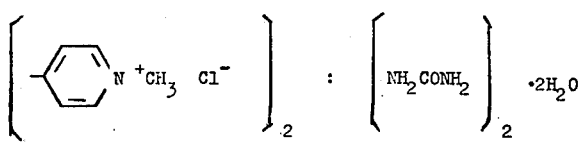

1,1′-Dimethyl-4,4′-bipyridylium dichloride (1.0 g.) was suspended in a mixture of hot ethanol and methanol (20 ml. and 10 ml. respectively). Urea (2.0 g.) was added to this solution, and on cooling white crystals were deposited. The crude product was recrystallised to constant melting behaviour from ethanol-methanol to yield 1.0 g. of pure crystalline material. The melting point of the complex was found to be 180°–200°C. The results of the elemental analysis of the complex were as follows:

Found: C, 40.9; H, 6.4; N, 19.2; Cl, 17.4%. The above formula requires: C, 40.7; H, 6.3; N, 20.3; Cl, 17.2%.

EXAMPLE 6

This Example illustrates the preparation of 1,1′-dimethyl-4,4′-bipyridylium dichloride: urea having the formula:

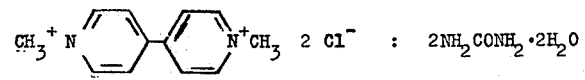

1,1′-Dimethyl-4,4′-bipyridylium dichloride (12.85 g.) and urea (6.0 g.) were dissolved together in water (10 ml.) with slight warming. The solution was treated with charcoal, filtered, and set aside for several days. The crystals which separated were collected, washed quickly with ice cold water, and dried in air. The yield of the complex was 4 g.

Found: C, 40.3; H, 5.8; N, 20.7. 1,1′-dimethyl-4,4′-bipyridylium ion 45.1%. $C_{14}H_{22}Cl_2N_6O_2.2H_2O$. The above formula requires: C, 40.7; H, 6.3; N, 20.3. 1,1′-dimethyl-4,4′-bipyridylium ion, 45.0%.

EXAMPLE 7

This Example illustrates the preparation of 1,1′-dimethyl-4,4′-bipyridylium dichloride:urea having the formula:

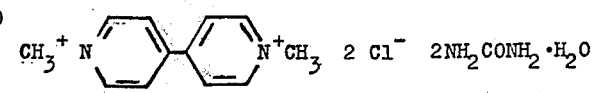

1,1′-Dimethyl-4,4′-bipyridylium dichloride dihydrate (10.6 kg.) dissolved in methyl alcohol (18 liters) was heated under reflux while urea (8.65 kg.) was added. Refluxing was continued for a further 30 minutes and ethyl alcohol (9 liters) was then added. After a further 30 minutes refluxing the solution was allowed to cool and the separated solid (13 kg.) collected. This solid was recrystallised by dissolving it in methyl alcohol (30 liters) heated under reflux, adding ethyl alcohol (15 liters) and allowing the solution to cool. The solid which separated (10.8 kg.) was collected and dried in air.

Found: C, 42.9; H, 6.1; N, 21.4. 1,1′-dimethyl-4,4′-bipyridylium ion 47.0%. $C_{14}H_{22}Cl_2N_6O_2.2NH_2CONH_2.H_2O$. The above formula requires: C, 43.1; H, 6.2; N, 21.5; 1,1′-dimethyl-4,4′-bipyridylium ion 47.1%.

EXAMPLE 8

This Example illustrates the preparation of 1,1′-di-2-hydroxyethyl-4,4′-bipyridylium dichloride:urea having the formula:

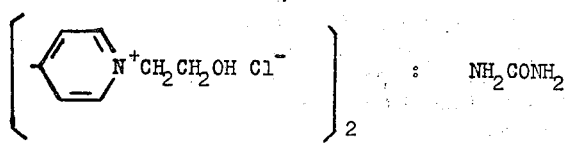

1,1'-Di-2-hydroxyethyl-4,4'-bipyridylium dichloride (2.0 g.) was dissolved in hot ethanol (20 ml.) with a small quantity of water added (less than 1 ml.). Urea (1.2 g.) dissolved in hot ethanol (10 ml.) was added, and the resultant solution cooled. Crystals of the unreacted diquaternary salt were first deposited, but on standing and the addition of a further small quantity of ethanol, white feathery crystals of the complex then separated. The yield of the complex was 1.0 g. and its melting point was determined as 184°–186°C. The results of the elemental analysis of the complex were as follows:

Found: C, 47.4; H, 5.9; N, 15.5%. The above formula requires: C, 47.7; H, 5.8; N, 15.0%.

EXAMPLE 9

This Example illustrates the preparation of 1,1'-bis-3,5-dimethylmorpholinocarbonyl-methyl-4,4'-bipyridylium dichloride:urea having the formula:

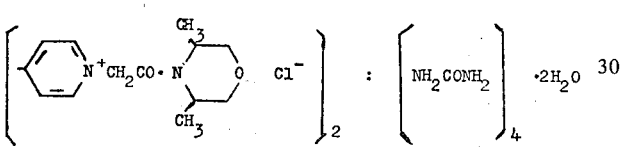

1,1'-Bis-3,5-dimethylmorpholinocarbonylmethyl-4,4'-bipyridylium dichloride (2.0 g.) was suspended in a mixture of hot ethanol and methanol (20 ml. and 10 ml. respectively). Urea (1.0 g.) was added, producing a solution which initially was coloured blue, but which rapidly faded to yield a yellow solution on cooling. The total solvent volume was reduced by evaporation to about one half, whereupon white crystals separated out. The yield of the complex was 1.0 g. and its melting point was found to be 154°–156°C. This complex was recrystallised from a small quantity of ethanol. The results of the elemental analysis of the complex were as follows: Found: C, 44.4; H, 6.8; N, 21.2; Cl, 8.2%. The above formula requires: C, 44.2; H, 6.8; N, 20.6; Cl, 8.6%.

EXAMPLE 10

This Example illustrates as another aspect of the invention the lower corrosivity of the urea and/or thiourea complexes of bipyridylium salts as compared with the corrosivity of the bipyridylium salts themselves. The test used to determine the amount of corrosion caused by a solution of the compound under investigation was carried out as follows: A rectangular strip of sheet aluminum measuring approximately 3/2 inches by ¼ inch was immersed to two-thirds of its length in a solution of the compound under test. Each test was carried out using a separate glass container in order to avoid electrolytic effects. The degree of corrosion caused by the test compounds in solution was assessed visually after 30 minutes. In the Table below, the amount of corrosion caused by a solution of bipyridylium salt complex has been expressed as a percentage of the corrosion caused by a solution of uncomplexed bipyridylium salt of the same concentration. Thus, for example, the FIG. 10 opposite the thiourea complex means that the solution of this complex caused corrosion to the extent of 10% of that produced by a solution of the uncomplexed bipyridylium ion of the same concentration.

| Complex | Percentage concentration of bipyridylium cation in solution | Amount of corrosion as a percentage of that caused by uncomplexed bipyridylium salt |
| --- | --- | --- |
| 1,1'-dimethyl-4,4'-bipyridylium dichloride: thiourea | 5 | 10 |
| " | 10 | 10 |
| 1,1'-dimethyl-4,4'-bipyridylium dichloride: urea | 5 | 40 |
| " | 10 | 90 |
| 1,1'-ethylene-2,2'-bipyridylium dichloride: thiourea | 5 | 15 – 20 |
| " | 10 | 15 – 20 |
| 1,1'-ethylene-2,2'-bipyridylium dibromide: thiourea | 5 | 50 – 75 |
| " | 10 | 40 – 60 |
| 1,1'-ethylene-2,2'-bipyridylium dibromide: urea | 5 | 30 – 50 |
| " | 10 | 40 – 60 |
| 1,1'-di-2-hydroxyethyl-4,4'-bipyridylium dichloride:thiourea | 10 | 30 |

It is evident from the above Table that complexing bipyridylium salts with urea or thiourea results in a substantial degree of inhibition of corrosion.

The following Examples 11 and 12 illustrate as another aspect of the invention the discovery that when used as agents for killing plants, the complexes of 1,1'-dimethyl-44'-bipyridylium dichloride with urea or thiourea show improved biological efficiency in comparison with the uncomplexed compound.

The procedure used in the tests for evaluating the phytotoxic effect of these compounds was as follows. An aqueous solution containing 0.1% of the test compound was sprayed onto cocksfoot plants. The damage to the plants was assessed visually at intervals and expressed as a percentage. The rates of application of the test compound are expressed in terms of pounds of cation per acre.

EXAMPLE 11

Results of herbicide tests with 1,1'-dimethyl-4,4'-bipyridylium dichloride:thiourea complex.

| 1,1'-dimethyl-4,4'-bipyridylium dichloride:thiourea complex at 1/100 lb. cation per acre | 1,1'-dimethyl-4,4'-bipyridylium dichloride at 1/100 lb. cation per acre |
| --- | --- |
| Time of Assessment | Time of Assessment |

-continued

| 1,1'-dimethyl-4,4'-bipyridylium dichloride:thiourea complex at 1/100 lb. cation per acre | | 1,1'-dimethyl-4,4'-bipyridylium dichloride at 1/100 lb. cation per acre. | |
|---|---|---|---|
| After Spraying | % damage | After Spraying | % damage |
| 3 weeks | 63 | 3 weeks | 58 |
| 4 weeks | 63 | 4 weeks | 51 |
| Complex at 1/50 lb. cation per acre. | | 1,1'-dimethyl-4,4'-bipyridylium cation at 1/50 lb. per acre. | |
| 4 weeks | 78 | 4 weeks | 76 |
| 6 weeks | 69 | 6 weeks | 62 |

The above Table shows that the thiourea complex gave approximately the same level of control as the uncomplexed bipyridylium salt initially, but the former persisted for a longer period.

EXAMPLE 12

Results of herbicide tests with 1,1'-dimethyl-4,4'-bipyridylium dichloride:urea complex.

| Bipyridylium compound | Rate of Application | % damage | | | | |
|---|---|---|---|---|---|---|
| | | 2 dys | 1 wk | 2 wks | 3 wks | 4 wks |
| Urea complex | 1/50 lb. cation | 55 | 80 | 87 | 89 | 85 |
| 1,1'-dimethyl-4,4'-bipyridylium dichloride | 1/50 lb. cation | 34 | 53 | 71 | 59 | 46 |

It is evident from the above Table that the complex produces a higher level of herbicidal activity, attained more rapidly, and lost more slowly than the uncomplexed bipyridylium salt.

The following Examples 13 and 14 illustrate as another aspect of the invention the preparation of solid compositions containing an inert salt in addition to urea or thiourea.

EXAMPLE 13

A hot solution (2.5 ml.) of 1,1'-dimethyl-4,4'-bipyridylium dichloride (containing 30% weight of 1,1'-dimethyl-4,4'-bipyridylium cation) was mixed with thiourea (1.4 g.) and anhydrous magnesium sulphate (3.3 g.). The solution solidified rapidly. A sample of this material was dried at 80° and it was found that the loss in weight was equal to the weight of water calculated to be originally present in the mixture.

EXAMPLE 14

A hot solution (2.5 ml.) of 1,1'-dimethyl-4,4'-bipyridylium dichloride (containing 30% by weight of 1,1'-dimethyl-4,4'-bipyridylium ion) was mixed with urea (1.4 g.) and anhydrous magnesium sulphate (0.77 g.). The solution solidified rapidly. A sample of this material was dried at 80° and it was found that the loss in weight was equal to the weight of water calculated to be originally present in the mixture.

EXAMPLE 15

This Example illustrates the preparation of a solid composition containing a solid complex of a herbicidal bipyridylium salt and a wetting agent.

A hot solution (2.5 ml.) of 1,1'-dimethyl-4,4'-bipyridylium dichloride (containing 30% by weight of the herbicidal cation) was mixed with 0.2 g. of a wetting agent sold under the same name of 'LISSAPOL' NX (LISSAPOL is a Registered Trade Mark). Urea (1.4 g.) and anhydrous magnesium sulphate (0.77 g.) were then dissolved in the solution. The solution solidified on standing for a short time.

What is claimed is:

1. A solid crystalline, essentially dry complex of a herbicidal bipyridylium salt selected from the group consisting of
   1,1'-ethylene-2,2'-bipyridylium dibromide,
   1,1'-dimethyl-4,4'-bipyridylium dichloride,
   1,1'-di-2-hydroxyethyl-4,4'-bipyridylium dichloride,
   1,1'-bis-3,5-dimethylmorpholinocarbonylmethyl-4,4'-bipyridylium dichloride,
   1-(2-hydroxyethyl)-1'-methyl-4,4'-bipyridylium dichloride,
   1,1'-di-carbamoylmethyl-4,4'-bipyridylium dichloride,
   1,1'-di-N-methylcarbamoylmethyl-4,4'-bipyridylium dichloride,
   1,1'-bis-N,N-dimethylcarbamoylmethyl-4,4'-bipyridylium dichloride,
   1,1'-diacetonyl-4,4'-bipyridylium dichloride, 1,1'-diethoxycarbonylmethyl-4,4'-bipyridylium dibromide, and
   1,1'-diallyl-4,4'-bipyridylium dibromide in combination with urea or thiourea, said complex having the formula $X(A)_n (H_2O)_m$, wherein X represents the bipyridylium salt, A represents a compound selected from urea and thiourea, n is selected from the integers 1, 2, and 4 and m is 0 or an integer of from 1–4, any water in said complex being present as lattice hydration.

2. A solid complex according to claim 1, in which X is a 1,1'-dimethyl-4,4'-bipyridylium dichloride, A is urea, and n is 2.

3. A solid complex according to claim 1, in which X is a 1,1'-dimethyl-4,4'-bipyridylium dichloride, A is thiourea, and n is 4.

4. A process of preparing a solid crystalline, essentially dry complex of a herbicidal bipyridylium salt selected from the group consisting of
   1,1'-ethylene-2,2'-bipyridylium dibromide,
   1,1'-dimethyl-4,4'-bipyridylium dichloride,
   1,1'-di-2-hydroxyethyl-4,4'-bipyridylium dichloride,
   1,1'-bis-3,5-dimethylmorpholinocarbonylmethyl-4,4'-bipyridylium dichloride, 1-(2-hydroxyethyl)-1'-methyl-4,4'-bipyridylium dichloride,
1,1'-di-carbamoylmethyl-4,4'-bipyridylium dichloride,
1,1'-di-N-methylcarbamoylmethyl-4,4'-bipyridylium dichloride,
1,1'-bis-N,N-dimethylcarbamoylmethyl-4,4'-bipyridylium dichloride,
1,1'-diacetonyl-4,4'-bipyridylium dichloride,
1,1'-diethoxycarbonylmethyl-4,4'-bipyridylium dibromide, and
1,1'-diallyl'4,4'-bipyridylium dibromide in combination with urea or thiourea, said complex having the formula X(A)$_n$ (H$_2$O)m, wherein X represents the bipyridylium salt, A represents a compound selected from urea and thiourea, $n$ is selected from the integers 1, 2, and 4 and $m$ is O or an integer of from 1–4, any water in said complex being present as lattice hydration, which comprises adding urea or thiourea to a heated solution of said bipyridylium salt in which the concentration of bipyridylium cation is a least 10% on a grams per milliliter basis and separating and drying the resulting crystalline complex so that any water therein is present as lattice hydration.

5. A process according to claim 4 which includes adding a salt which is capable of acquiring water of crystallization to said solution.

6. A solid, crystalline, essentially dry herbicidally effective complex of a herbicidal salt of the 1,1'-dimethyl- 4,4'-bipyridylium cation having the structure:

in combination with urea or thiourea, said complex having the formula X(A)$_n$(H$_2$O)$_m$, wherein X represents the 1,1'-dimethyl-4,4'-bipyridylium salt, A represents a compound selected from urea or thiourea, $n$ is selected from the integers 1, 2 and 4 and $m$ is O or an integer from 1 to 4.

* * * * *